(12) United States Patent
Krasnykh

(10) Patent No.: US 9,326,366 B2
(45) Date of Patent: Apr. 26, 2016

(54) INTRA PULSE MULTI-ENERGY METHOD AND APPARATUS BASED ON RF LINAC AND X-RAY SOURCE

(71) Applicant: The Board of Trustees of the Leland Stanford Junior University, Palo Alto, CA (US)

(72) Inventor: Anatoly Krasnykh, Santa Clara, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 221 days.

(21) Appl. No.: 14/213,372

(22) Filed: Mar. 14, 2014

(65) Prior Publication Data

US 2014/0270086 A1    Sep. 18, 2014

Related U.S. Application Data

(60) Provisional application No. 61/783,082, filed on Mar. 14, 2013.

(51) Int. Cl.

| | |
|---|---|
| *H05G 2/00* | (2006.01) |
| *H05H 9/02* | (2006.01) |
| *H05H 7/22* | (2006.01) |
| *G01N 23/083* | (2006.01) |
| *H05H 7/02* | (2006.01) |
| *H05G 1/20* | (2006.01) |
| *G21K 5/00* | (2006.01) |
| *H05H 7/12* | (2006.01) |

(52) U.S. Cl.
CPC ............... *H05G 2/00* (2013.01); *G01N 23/083* (2013.01); *H05H 7/22* (2013.01); *H05H 9/02* (2013.01); *G21K 5/00* (2013.01); *H05G 1/20* (2013.01); *H05H 2007/025* (2013.01); *H05H 2007/122* (2013.01)

(58) Field of Classification Search
None
See application file for complete search history.

(56) References Cited

U.S. PATENT DOCUMENTS

| | | | | |
|---|---|---|---|---|
| 4,007,375 | A | 2/1977 | Albert | |
| 6,125,167 | A | 9/2000 | Morgan | |
| 7,130,371 | B2 * | 10/2006 | Elyan | H01J 35/14 315/505 |
| 7,208,889 | B2 * | 4/2007 | Zavadtsev | G21K 5/04 250/396 R |
| 8,183,801 | B2 | 5/2012 | Chen et al. | |
| 8,232,748 | B2 * | 7/2012 | Treas | H05H 7/02 250/390.1 |
| 8,311,187 | B2 | 11/2012 | Treas et al. | |
| 8,339,071 | B2 * | 12/2012 | Zavadtsev | G21K 5/04 250/396 R |
| 8,384,314 | B2 * | 2/2013 | Treas | H05H 7/02 250/390.1 |

(Continued)

FOREIGN PATENT DOCUMENTS

| | | |
|---|---|---|
| WO | WO 2011/071759 | 6/2011 |
| WO | WO 2012/054381 | 4/2012 |

*Primary Examiner* — Thomas R Artman
(74) *Attorney, Agent, or Firm* — Lumen Patent Firm

(57) ABSTRACT

The relative position of an RF waveform and electron bunches in a linear accelerator is controlled by appropriate control of the accelerator electronics. Thus the energy given to any particular electron bunch can be controlled by altering the position of amplitude peaks of the RF driving field relative to the electron bunch. This control can be applied simultaneously and independently to all electron bunches in a bunch train. An output X-ray pulse is provided by the contributions of multiple electron bunches when they hit one or more targets. When more energetic electrons hit the target, more energetic X-rays are produced. Thus this controllable electron bunch energy and intensity can provide intra-pulse control of X-ray energy.

3 Claims, 14 Drawing Sheets

(56) References Cited

U.S. PATENT DOCUMENTS

| | | | |
|---|---|---|---|
| 8,457,274 B2 | 6/2013 | Arodzero et al. | |
| 8,541,756 B1* | 9/2013 | Treas | G01N 23/09 250/390.01 |
| 2005/0205772 A1* | 9/2005 | Zavadtsev | G21K 5/04 250/251 |
| 2006/0050746 A1* | 3/2006 | Elyan | H01J 35/14 372/10 |
| 2007/0140422 A1* | 6/2007 | Elyan | H01J 35/14 378/57 |
| 2010/0188027 A1* | 7/2010 | Treas | H05H 7/02 315/505 |
| 2010/0195791 A1 | 8/2010 | Ishkhanov et al. | |
| 2011/0206179 A1 | 8/2011 | Bendahan | |
| 2012/0081042 A1 | 4/2012 | Cheung et al. | |
| 2012/0206069 A1* | 8/2012 | Zavadtsev | G21K 5/04 315/501 |
| 2012/0294423 A1 | 11/2012 | Cheung et al. | |
| 2013/0016814 A1* | 1/2013 | Treas | H05H 7/02 378/106 |
| 2014/0270086 A1* | 9/2014 | Krasnykh | H05G 2/00 378/124 |

* cited by examiner

INTRA PULSE MULTI-ENERGY METHOD AND APPARATUS BASED ON RF LINAC AND X-RAY SOURCE

CROSS REFERENCE TO RELATED APPLICATIONS

This application claims the benefit of U.S. provisional patent application 61/783,082, filed on Mar. 14, 2013, and hereby incorporated by reference in its entirety.

FIELD OF THE INVENTION

This invention relates to X-ray sources.

BACKGROUND

A radiographic method with an X-ray source is usually the most cost effective method for container inspection. Traditional methods include generation of an electron beam, accelerating the beam energy, decelerating the electrons in a target thereby producing an X-ray beam, forming a spatial X-ray field that illuminates a container, and analyzing the X-ray photons with a detector array.

Recently, detection systems for X-ray cargo systems that can make use of multi-energy X-ray pulses have been considered, e.g., in U.S. Pat. No. 8,457,274 and in WO 2012/054381. Although the X-ray sources considered in this work provide multi-energy X-ray pulses, these multi-energy X-ray pulses do not have fully controllable intra-pulse energies.

Accordingly, it would be an advance in the art to provide X-ray pulses with full control over intra-pulse energy.

SUMMARY

The basis of the present approach is a specific operating mode (and corresponding apparatus) of an RF (radio frequency) linear accelerator (linac). More specifically, the relative position of an RF waveform and electron bunches in a linear accelerator is controlled by appropriate control of the accelerator electronics. Since the electron bunches and the RF waveform travel at substantially the same speed, for relativistic electron bunches, such control has the effect of controlling the amount of energy provided to the electron bunches by the RF waveform. The energy given to any particular electron bunch can be controlled by altering the position of amplitude peaks of the RF driving field relative to the electron bunch. This control can be applied simultaneously and independently to all electron bunches in a bunch train.

For the implementation of intra-pulse energy control, a traveling wave (TW) accelerating structure fed by a klystron-based RF source is better suited than the magnetron based linac with a standing wave structure. In this case the required intra-pulse multi-energy capability can be achieved by varying the amplitude and/or the phase of the RF source during the pulse, thus causing the klystron output to slide up or down on the resonance curve or by ramping the drive level of the klystron by adjusting the output of the sub-booster of the klystron. Either method requires us to vary the phase and/or amplitude relation between the electron bunch position and the RF wave during the pulse.

An output X-ray pulse is provided by the contributions of multiple electron bunches when they hit one or more targets. When more energetic electrons hit the target, more energetic X-rays are produced. Thus the controllable electron bunch energy described above can provide intra-pulse control of X-ray energy.

Multiple targets can be employed to increase the total output X-ray pulse rate. Such increased output is important for applications, especially cargo screening. Nuclear charge (Z) and atomic weight (A) are the main parameters of a material to be detected in cargo screening. At least two X-ray energies are needed to increase the probability of correct identification. Conventional methods with two X-ray energies are based on pulse-to-pulse energy variation, i.e. electron beam energy is practically constant during one cycle of linac operation and it is changed for the next pulse. A disadvantage of this method is a limitation of the inspection speed.

In contrast, the present approach provides a controllable beam energy sweep during each pulse, which produces a time-spatial distribution of X-ray photons. Different materials possess different total cross sections of X-ray interactions due to different dependences of the Compton Effect, the photoelectric effect, and the pair-production effect on material composition. Having an intra-pulse energy sweep of X-ray photons increases the available information for identifying target materials.

Advantages include: (1) A high throughput (e.g., up to 60 km/h cargo speed) and (2) the high probability of unambiguous material identification.

A significant application of this work is in relation to cargo scanning (e.g., for port security). An X-ray source as described herein can produce ramping and controllable end-point energy during each pulse. The end point X-ray energy and flux intensity is controllable in such a way that a detector system can resolve the time-energy structure of the ramping pulse. This technical approach is based on fast detectors which can resolve the time-energy structure of the pulse. This approach provides the information needed for material discrimination in a single X-ray pulse. A single detector channel records the energy dependent attenuation in the course of a single X-ray pulse. Not only is there no penalty in penetration or in scan speed as in traditional dual energy systems, the method also provides a new flexibility in the choice of the energy bins.

Thus, for instance, when in a traditional 4/6 MeV interlaced dual energy system the 4 MeV pulse incident on the cargo is attenuated to a level which no longer allows material discrimination, the ramping pulse system of the present approach could use a 5/7 MeV energy bin combination for material discrimination. Relying on the relation of three energy bins for material discrimination is also possible. Furthermore, in the case of less attenuating cargo, the ramping energy pulse can be stopped as soon as sufficient signal has been recorded, thus minimizing the radiation created by the source to the amount needed for the radiograph.

If highly attenuating cargo is detected, the X-ray pulse energy can be increased to a maximum value which ensures the best possible penetration. If the maximum end-point energy is chosen to be high enough to induce photofission in special nuclear material (SNM), the resulting prompt neutrons and delayed gammas can be detected and activate a real-time alarm resolution. This is especially important for rail scanning as a secondary inspection when alarm resolution is not practical. Note, that this approach generates neutrons only during the very short time when the system calls for high-Z alarm resolution. Other scan scenarios could be realized with the present X-ray source. None of the current state of the art cargo scanning RF linacs have the capability to vary the electron beam during the pulse. Varying and controlling the electron beam current and energy during the duration of the pulse would allow the truly rapid scanning of cargo while it is in normal motion.

X-ray sources for cargo inspection employ the pulse mode of operation. Each cycle includes three intervals: (1) X-ray generation, (2) X-ray detecting and analysis, and (3) a residual/service period for storage of energy for the new cycle. The pulse mode of operation allows producing X-ray energy and intensity that are sufficient for cargo inspection. The repetition rate has a technical limitation to be less than 1000 pulses per second, i.e. a repetition rate period of 1 millisecond or more. Typically, the repetition rate is 400 Hz (i.e. the period is 2.5 milliseconds). The high power switches (thyratron, thyristor assembly, etc.) in the linac power supply are the main components that limit the repetition rate.

Dual beam energy concepts limit the speed of the cargo inspection. If we will require scanning each cm of cargo length, then a cargo velocity has to be less than 0.4 cm/sec (i.e. v<14.4 km/hr). Requirement for advanced cargo inspection may include a resolution of 5 mm. Maximum X-ray penetration in dual energy approach is realized with only the high energy pulse. There is a probability that an irradiation of a heavy density material will be in a period of the low energy pulse. One can see that the cargo velocity will be too low and a material identification process will take a long time because: (1) there is the pulse mode of operation; (2) the dual beam energy is needed for material identification; and (3) one target (X-ray converter) is used. The dual energy approach cannot perform material identification for items which are smaller than the distance of the cargo moved during the pulse separation.

The repetition rate in the intra-pulse multi-energy case is not increased. However (1) the number of X-ray converters (e.g., targets) can be more than one and (2) a controllable beam energy and intensity sweep can be realized on each target (converter). Basically the idea looks like the employment of an array of linacs. They are controllably working as a system on the separated targets. However the idea is embodied as a single X-ray source. The individual targets with their collimators form separated X-ray fan beams.

DETAILED DESCRIPTION

Figure 1A:
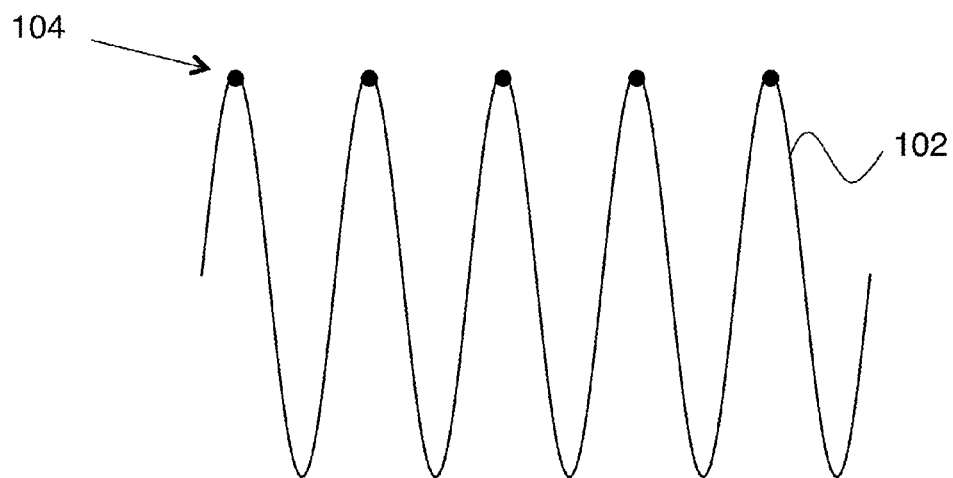
FIGS. 1A-C show examples of controlling the energy delivered to electron bunches by controlling the relative position of the electron bunches and an RF waveform.
Figure 1B:
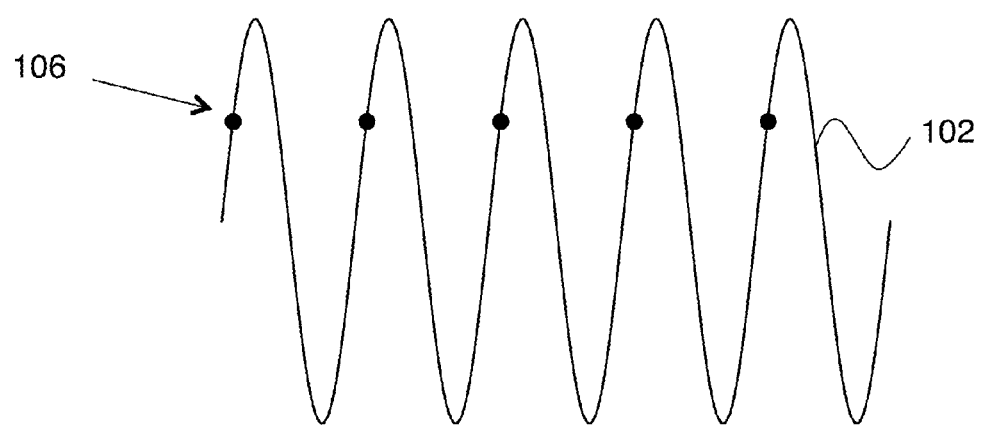
Figure 1C:
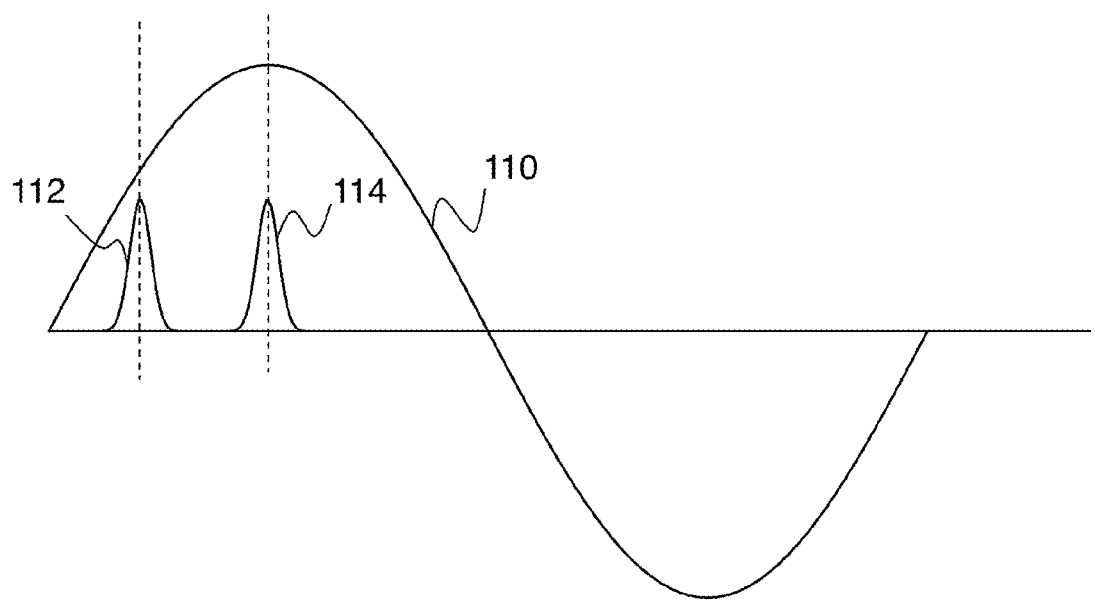

FIGS. 1A-C show examples of controlling the energy delivered to electron bunches by controlling the relative position of the electron bunches and an RF waveform. In the example of FIG. 1A, electron bunches 104 are at peaks of RF waveform 102, leading to maximum energy transfer from RF waveform 102 to electron bunches 104. In the example of FIG. 1B, electron bunches 104 are away from peaks of RF waveform 102, leading to reduced energy transfer from RF waveform 102 to electron bunches 104. In these examples, the RF waveform is not modulated, and has a period equal to the electron bunch spacing. Thus all bunches in a bunch train have substantially the same position relative to features of the RF waveform (e.g., peaks). The following examples show how more specific control of electron bunch energy can be provided by amplitude and/or phase modulation of the RF waveform.

FIG. 1C shows the basic idea. Here curve 110 is an electromagnetic wave that is propagated in the accelerating structure and curves 112 and 114 illustrate two different electron bunch phase positions versus the wave phase. Bunch position 112 has a bunch phase that leads to less energy than the bunch phase of bunch position 114. During a long RF pulse, bunches of different time intervals will be accelerated at the different energies. The phase sweep during the pulse is slow compared to RF cycle.

Figure 2A:
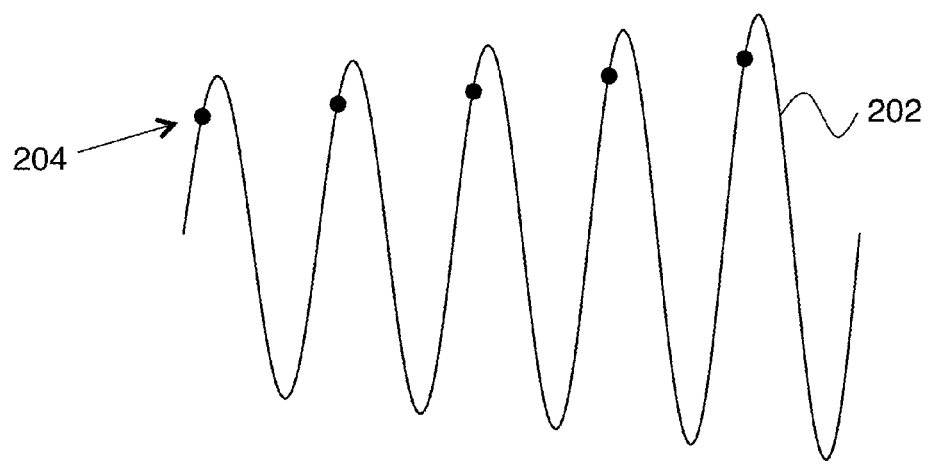
FIG. 2A shows an example of controlling the energy delivered to electron bunches by controlling the relative position of the electron bunches and an amplitude modulated RF waveform.

FIG. 2A shows an example of controlling the energy delivered to electron bunches by controlling the relative position of the electron bunches and an amplitude modulated RF waveform. In the example of FIG. 2A, electron bunches 204 get larger amounts of energy from left to right on the figure because of amplitude modulation of RF waveform 202.

Figure 2B:
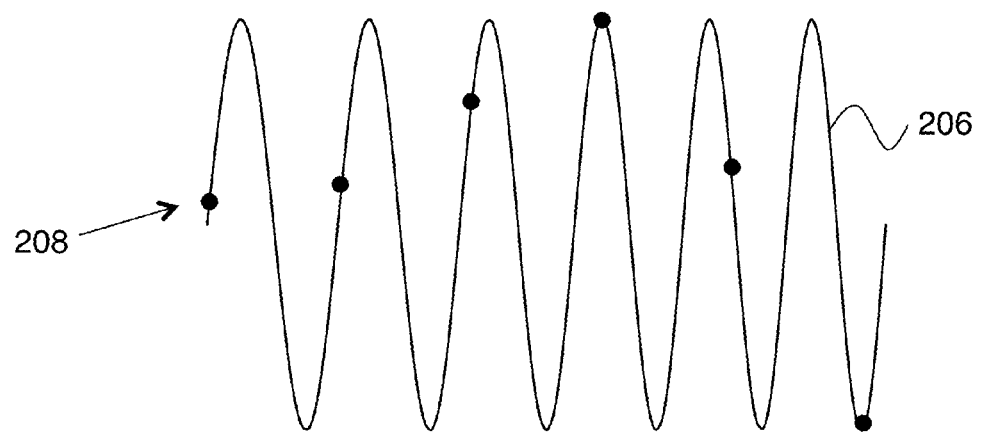
FIG. 2B shows an example of controlling the energy delivered to electron bunches by controlling the relative position of the electron bunches and a phase modulated RF waveform.

In the example of FIG. 2B, electron bunches 208 get variable amounts of energy from left to right on the figure because of phase modulation of RF waveform 206.

Figure 3A:
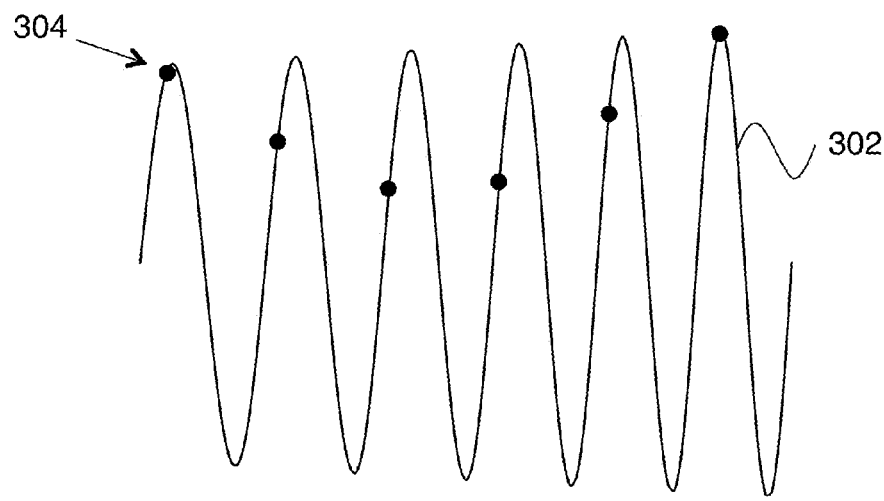
FIGS. 3A-B show examples of controlling the energy delivered to electron bunches by controlling the relative position of the electron bunches and an amplitude and phase modulated RF waveform.
Figure 3B:
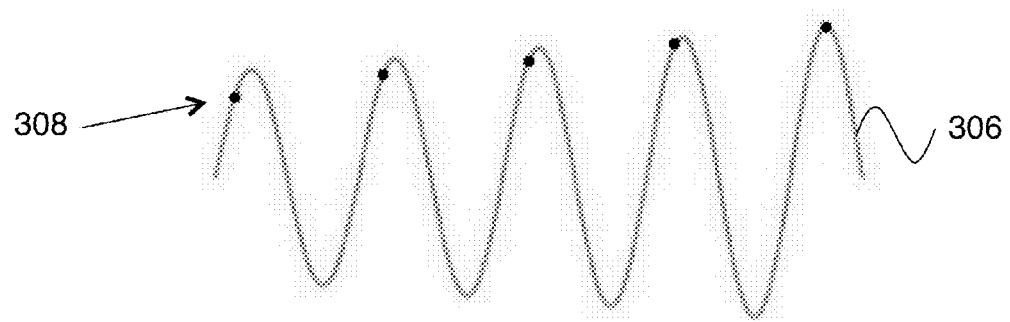

FIGS. 3A-B show examples of controlling the energy delivered to electron bunches by controlling the relative position of the electron bunches and an amplitude and phase modulated RF waveform. In the example of FIG. 3A, electron bunches 304 get variable amounts of energy from left to right on the figure because of amplitude and phase modulation of RF waveform 302. Similarly, in the example of FIG. 3B, electron bunches 308 get variable amounts of energy from left to right on the figure because of amplitude and phase modulation of RF waveform 306.

More specifically, FIG. 3B shows an example where several RF cycles 306 of the RF pulse have varying RF amplitude and phase with electron bunches 308 at each RF cycle. The electron bunch separation can be approximately one RF period and the RF/Xray pulse length can be 4 to 10 microseconds (~9000 to 28000 RF periods). Thus a single X-ray pulse has contributions from many electron bunches.

During a long RF pulse, many bunches will be accelerated, each at an energy according to the amplitude of its RF cycle. FIG. 3B shows only a portion of that long pulse. The amplitude sweep during the pulse (4 to 10 μs) is slow compared to the RF cycle itself. In an ideal case at the linac output, each bunch will possess its own energy during the pulse width. Modulation of the phase can be used as a vernier for additional amplitude variation by sliding up and down on the RF pulse itself in the vicinity of the crest. This will cause some phase shift between the bunch and the RF from one cycle to the next inside the pulse. Thus we can amplify or reduce the bunch to bunch beam energy control achieved only from amplitude variation by using also the phase control.

The range of the phase sweep is programmable and can be varied. The possible X-ray flux drop can be compensated for by varying the beam intensity from the gun using a feedback on the electron-gun grid voltage. Beam loading effects on the bunch train pulse can be compensated with feedback loops on the RF phase-amplitude controller.

Figure 4:
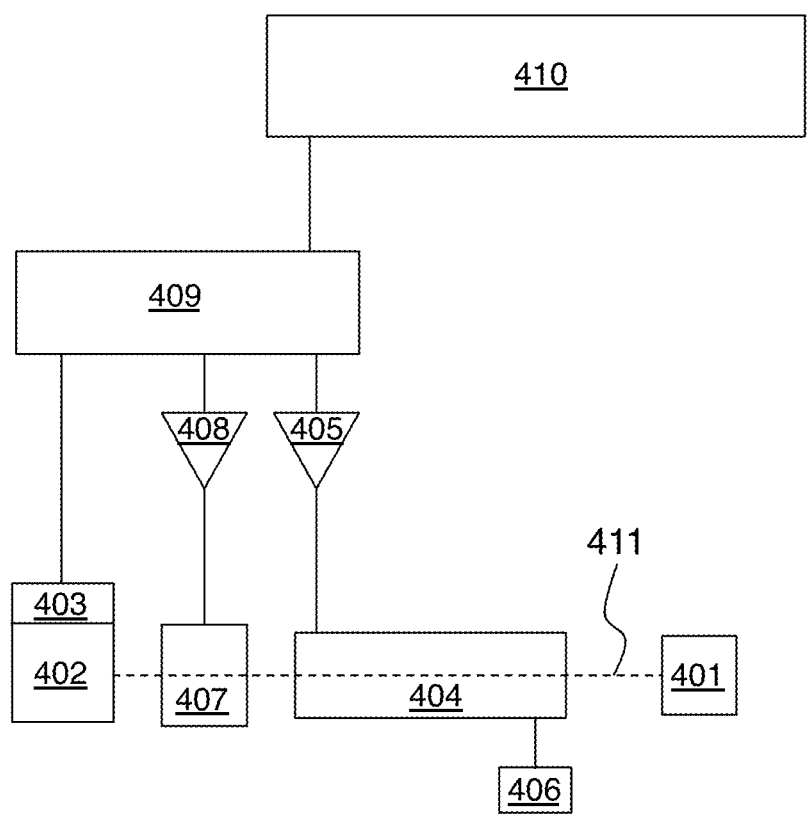
FIG. 4 is a block diagram of an exemplary embodiment of the invention.

FIG. 4 is a block diagram of an exemplary embodiment of the invention. For simplicity, the beam focusing system and modulator components are not shown. Here a control console 410 is connected to a master RF source and controller 409. Controller 409 is connected to beam current controller 403 which controls operation of electron source 402 (e.g., a gridded electron gun). Controller 409 is also connected to amplifier 408 that drives RF buncher 407. Finally, controller 409 is connected to amplifier 405 (e.g., a Klystron-based RF source) that provides the RF waveform for traveling-wave accelerating structure 404. At the output of accelerating structure 404, the remaining RF energy is dumped into RF load 406, while accelerated electron bunches 411 are incident on an electron beam to X-ray converter 401 (e.g., one or more targets). Practice of the invention does not depend critically on target composition or design.

The electron beam output of accelerator 404 can include a train of individual bunches which are separated by the RF source periods. The bunch energy and peak current of the train can be varied in such a way that the X-ray dose rate after converter 401 will stay practically constant during each pulse. Accomplishment of this mode of operation will require amplitude and phase modulation in the RF controller 409.

The temporal position of the individual electron bunches with respect to the accelerating RF waveform in the TW linac can be set and be controlled. The use of high gain and tunable components (e.g., 405 and 408 above) allows performing needed amplitude and phase modulation at a low level RF power with a programmable logic controller and/or a personal computer based technology. The bandwidth of the RF control system and feedback loops (i.e. the speed of the amplitude and phase change) can be matched with the bandwidth of the high power linac components. The conventional electron gun (typically used in X-Ray sources) includes an anode-cathode. In the present approach, a gridded electron gun configuration can be considered. The beam current amplitude can be set by a control of the grid potential during the pulse width. The output electron energy of the gun can be controlled by a grid-anode power supply. A separation of the gun output energy from the gun beam intensity can optimize the beam loading compensation in the accelerating structure. In this case, the gun beam intensity controller will communicate with the master RF source and RF controller 409. The intra-pulse beam intensity control ability will enable adaptively controlling the X-ray dose rate during each X-ray pulse. A production cost of this X-ray source with the intra pulse multi energy scan will be not dramatically increased compared to the cost of magnetron based X-ray machines.

In order to take advantage of bunch by bunch energy variation amplification or reduction with phase modulation, electron bunches are preferably as short as possible so that the energy spread when they are not at the crest of the RF is minimized. For this purpose and also to assure a controlled transmission through the accelerator to the target, we would like bunches to be as short as possible. Additionally, the very low electron beam energy from the gun has to be increased to a level where the beam is traveling at nearly the speed of light in order for it to be synchronized with the RF in the main accelerator section. Preferably a bunching system upstream of the speed of light accelerator structure is used to achieve short bunches that can be fed into the accelerator structure.

Figure 5:
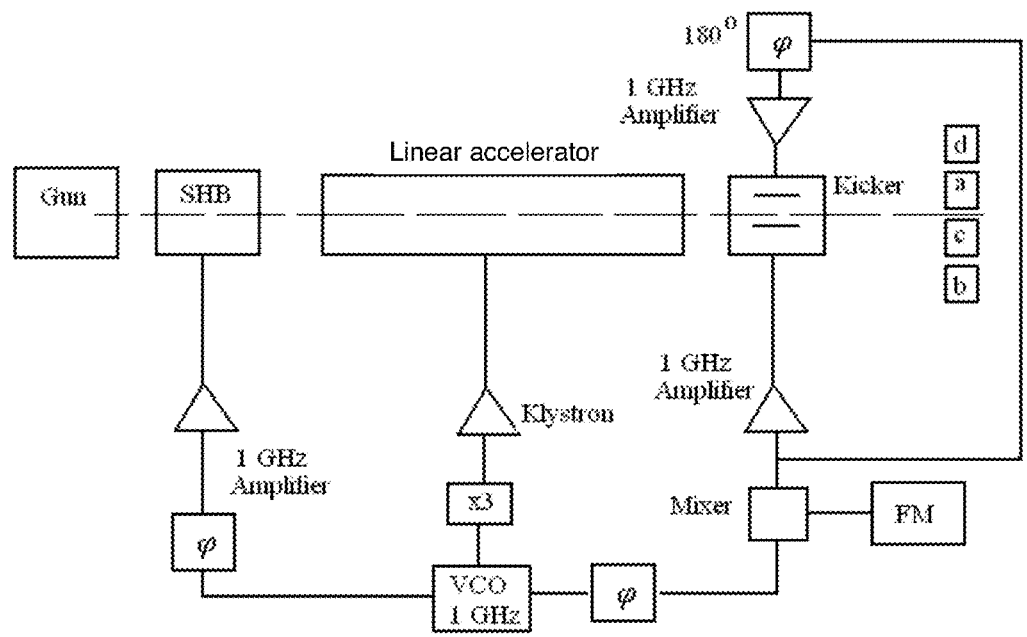
FIG. 5 is another exemplary block diagram.

FIG. 5 is another exemplary block diagram. In this example, a 3 GHz standing-wave linac is employed as the accelerating structure. A 1 GHz sub harmonic cavity (SHB) is used for longitudinal beam bunching. Phase modulation at f=1 GHz (by FM system) is provided, which can be programmable. A kicker with 1 GHz amplifiers possess enough bandwidth to manipulate the phase modulation. The main reason for using sub-harmonic bunching in this case is to increase the beam intensity, since higher beam intensities can be used for a standing-wave linac if subharmonic bunching (e.g., $F_{bunch}=F_{RF}/N$) is used than if $F_{bunch}=F_{RF}$.

Here the electron beam to X-ray converter (i.e., 401 on FIG. 4) includes a kicker and four targets a, b, c, and d. The kicker periodically distributes incoming electron bunches to the four targets (in general, any number of targets can be employed, and the kicker would distribute incoming electron bunches to the N targets). A repetition rate of the electron bunches is preferably N times a repetition rate of the kicker. For example, if F_train is the frequency of the electron bunch train, and F_kick is the frequency of the kicker, then F_train=N*F_kick.

Figure 6:
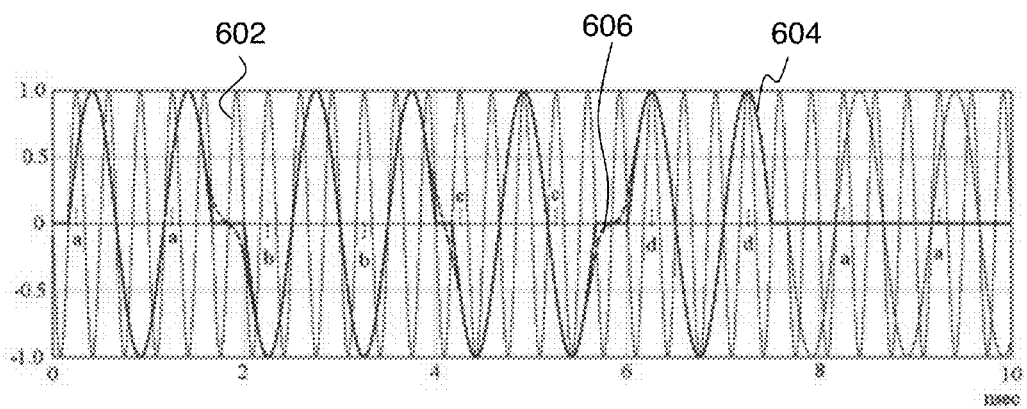
FIG. 6 shows exemplary operation of a kicker for distributing electron bunches to multiple targets.

FIG. 6 shows exemplary operation of a kicker for distributing electron bunches to multiple targets. More specifically, FIG. 6 shows one period of the beam distribution for four targets. This period is a very small time (note that the horizontal time axis is 10 nsec long). The targets are labeled as "a", "b", "c", and "d". This concept is feasible: it is not hard for the low level electronic system and it is not hard work for the 1 GHz amplifiers because a "fast" distortion of the RF power is not unduly troublesome, i.e. the bandwidth of the 1 GHz amplifiers is reasonable.

Waveform 602 is a 3 GHz RF waveform. The accelerating structure is filled by this oscillation. Trace 604 is kicker amplitude vs. time for one plate. The kicker includes two plates which act on the beam bunches in differential mode. A differential mode is created by a 180 degree phase shifter as shown in FIG. 5. A separation between the bunches is 1 nsec. The position of bunches is marked by "a", "b", "c", or "d" on the time axis. One can see that kicker amplitude is +50% for "a" bunches. The kicker amplitude is −100% for "b" bunches. It goes to −50% for the "c" bunches, and it is +100% for the "d" bunches. After 8 nsec a sequence of the beam distribution is repeated. One can mention that in this design the total beam current is three times lower because the train has a bunch separation equal to 1 nsec (which is 3× greater than the period of waveform 602). However this disadvantage can be fixed if the gun perveance is chosen accordingly (for the given gun voltage it should be three times higher). A gun mode optimization for this case is possible.

Trace 604 (kicker amplitude vs. time, solid line) is shown for an ideal case. In reality the kicker waveform will include transients (dashed lines, referenced as 606) as shown on FIG. 6. One can see that the 1 GHz RF distortion is not excessive. A Q-factor for the TEM-mode kicker is equal to 1. The length of the kicker plates for the TEM mode kicker will be longer. However thanks to a small distortion of the 1 GHz power, an RF-cavity with the transverse electric field can be used in this case. The reasonable Q-factor can be used to reduce the required RF power of 1 GHz amplifier. A reasonable distortion depends on the beam patterns on X-ray targets.

Figure 7A:
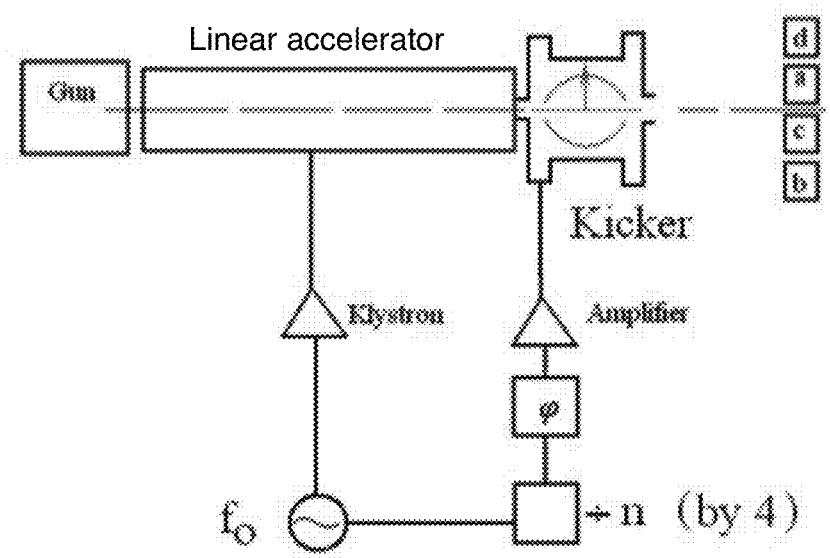
FIGS. 7A-B show an exemplary kicker configuration.
Figure 7B:
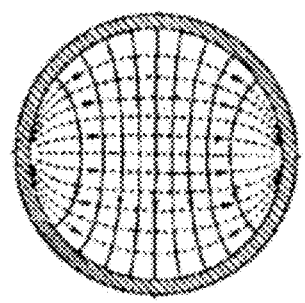

FIGS. 7A-B show an exemplary kicker configuration. This example is based on employment of the TE11 mode in a cylindrical cavity for the kicker. The cavity is placed at the linac end and a subharmonic frequency is used to excite it. A simplified sketch of this approach is shown on FIG. 7A, and the field pattern in the kicker is shown on FIG. 7B.

Figure 8A:
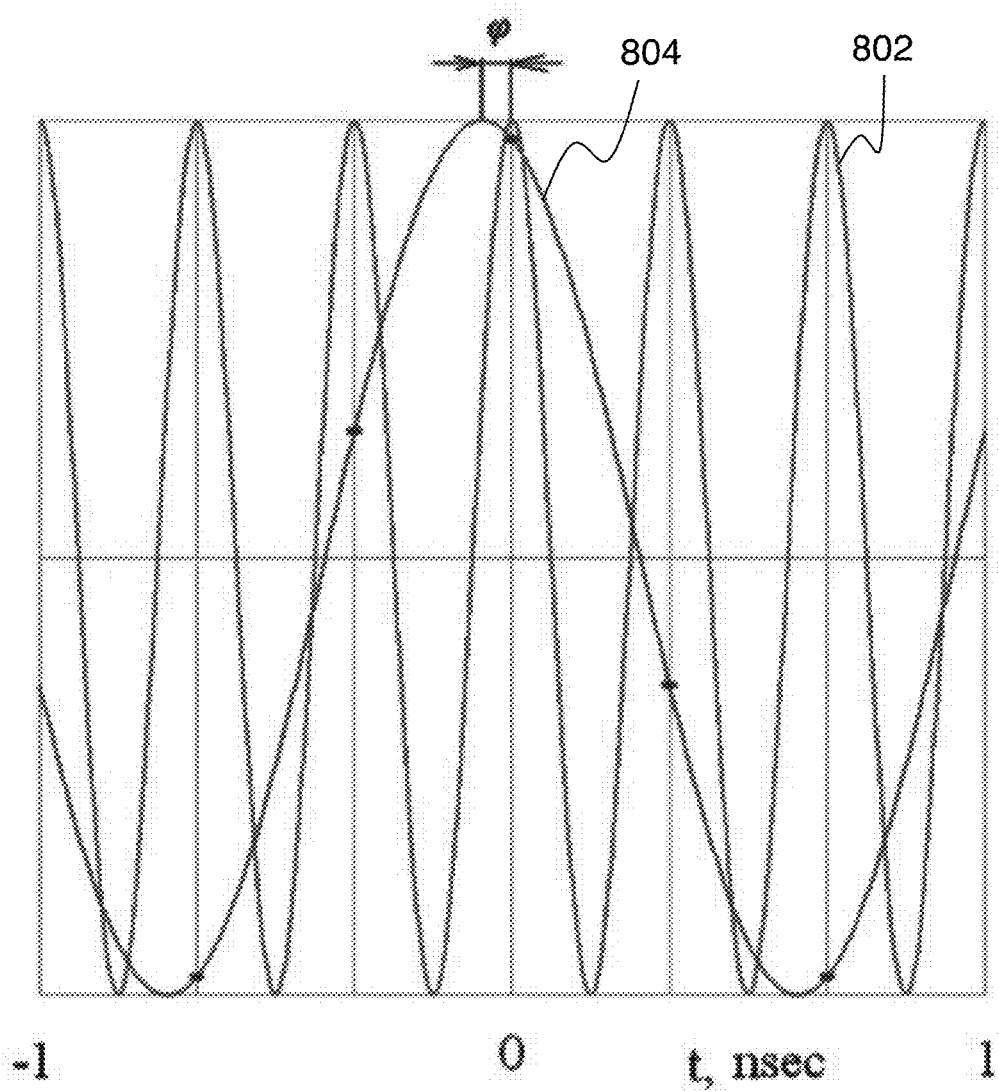
FIGS. 8A-B show exemplary electron bunch/RF waveform relative positions.
Figure 8B:
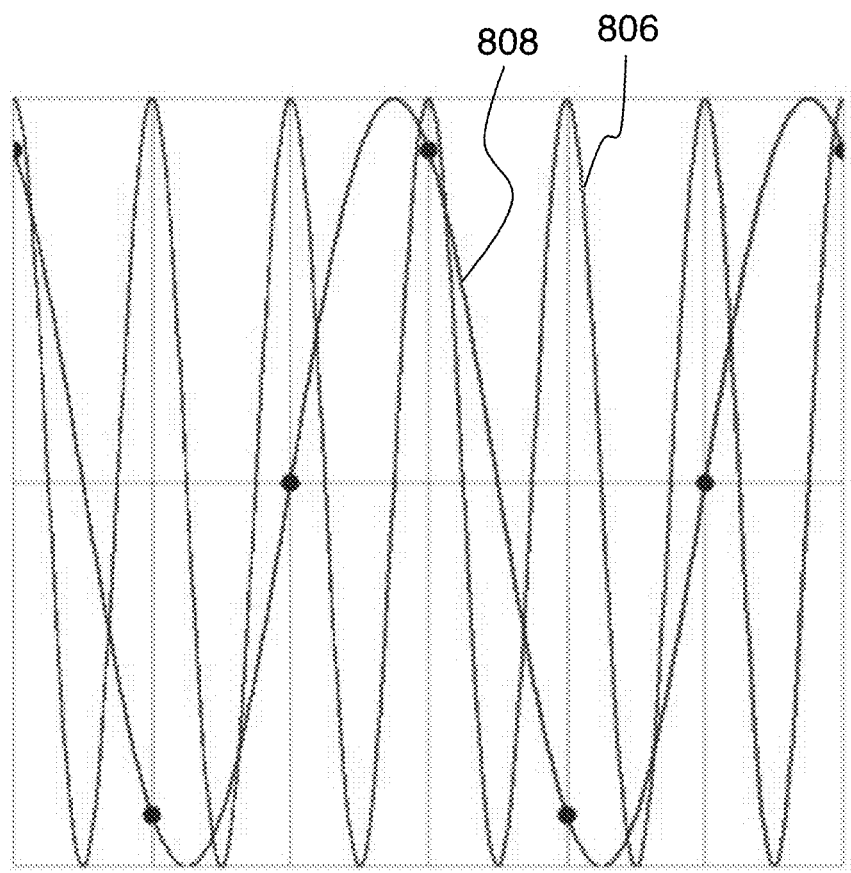

FIGS. 8A-B show exemplary electron bunch/RF waveform relative positions. FIG. 8A shows a kicker field in the cylindrical cavity (804) and the accelerating RF field (802) for the case of beam separation for four targets. Four targets will require a 750 MHz RF source for the kicker cavity, assuming a 3 GHz accelerating RF frequency. The black dots in FIG. 8A illustrate positions of electron bunches vs. time and show relative kick amplitudes for a phase shift $\phi=\pi/8$. In this case the normalized kicker amplitudes on each period of sub harmonic frequency will be 0.924, −0.383, −0.924, and 0.383 accordingly. One can see that the target separation is not equidistant. Another feature of this case is the following fact: A phase shift of $\phi=\pi/4$ will split the beam in two parts, which gives normalized kicker amplitudes of ±0.71. FIG. 8B relates to a design for three targets, which will require employing a 1 GHz RF source for the kicker, still assuming a 3 GHz accelerating RF frequency. An outside diameter of the kicker cavity in this case will be smaller. Waveforms of the RF carrier 806 (at 3 GHz) and its sub-harmonic 808 (at 1 GHz) are shown. The required phase shift here is $\phi=\pi/6$. A kicker cavity where the RF field has an azimuthal rotation can also be designed. For this case the targets are situated equidistant on a circumference.

Figure 9:
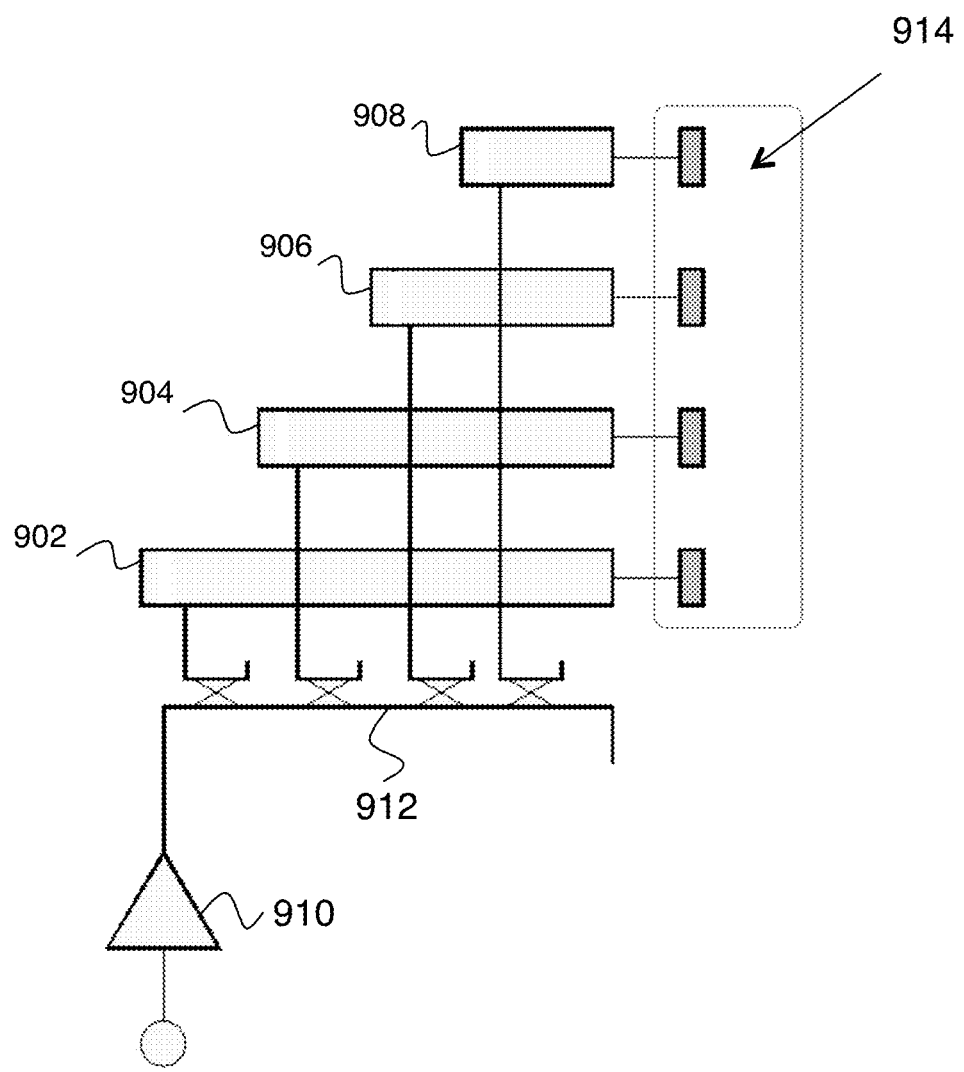
FIG. 9 shows another multi-target embodiment.

FIG. 9 shows another multi-target embodiment. In this example, multiple accelerators 902, 904, 906 and 908 are fed from a single controllable source 910 and distribution network 912 in order to provide X-rays from multiple targets 914. Here the longer accelerators can have larger operating powers (e.g., 3 MW, 2 MW, 1.2 MW and 0.6 MW for 902, 904, 906, and 908 respectively). Higher operating powers will lead to higher output electron beam energy, which is proportional to the square root of the operating power. Each accelerator is separately optimized for its electron beam energy range. Electron beam outputs can be focused by common focusing elements for various energy ranges (e.g., C-band, X-band).

Figure 10:
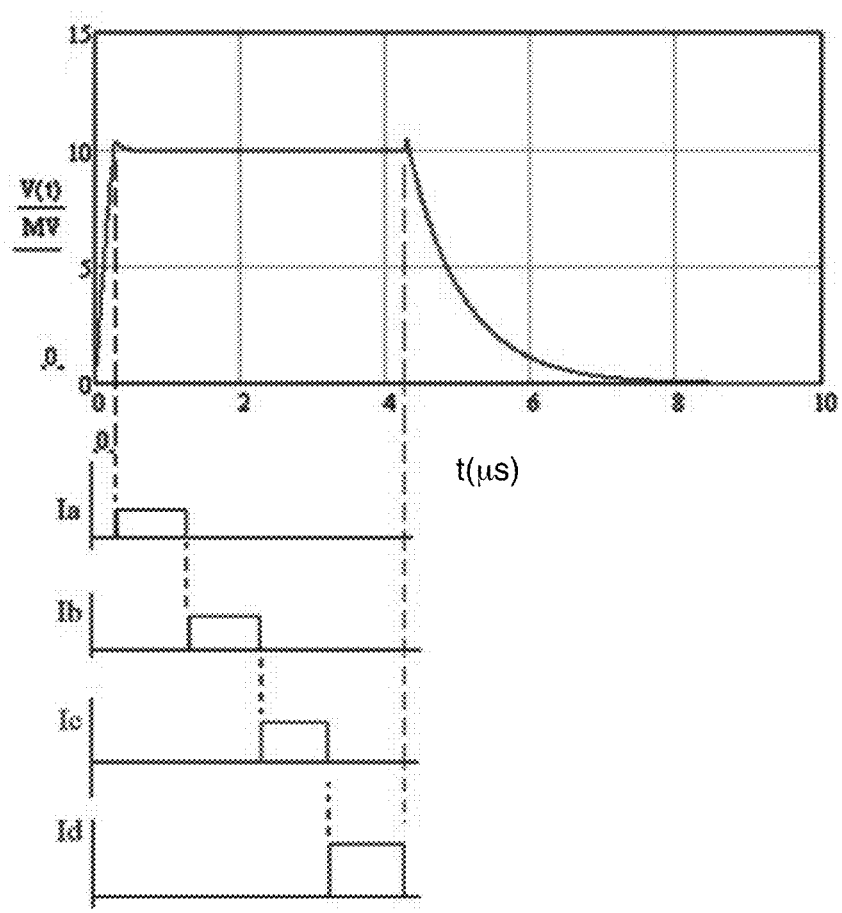
FIG. 10 shows a timing diagram relating to the example of FIG. 9.

FIG. 10 shows a timing diagram relating to the example of FIG. 9. Here it is shown how the different accelerators can each contribute to a different time slice of the total accelerator output.

Figure 11:
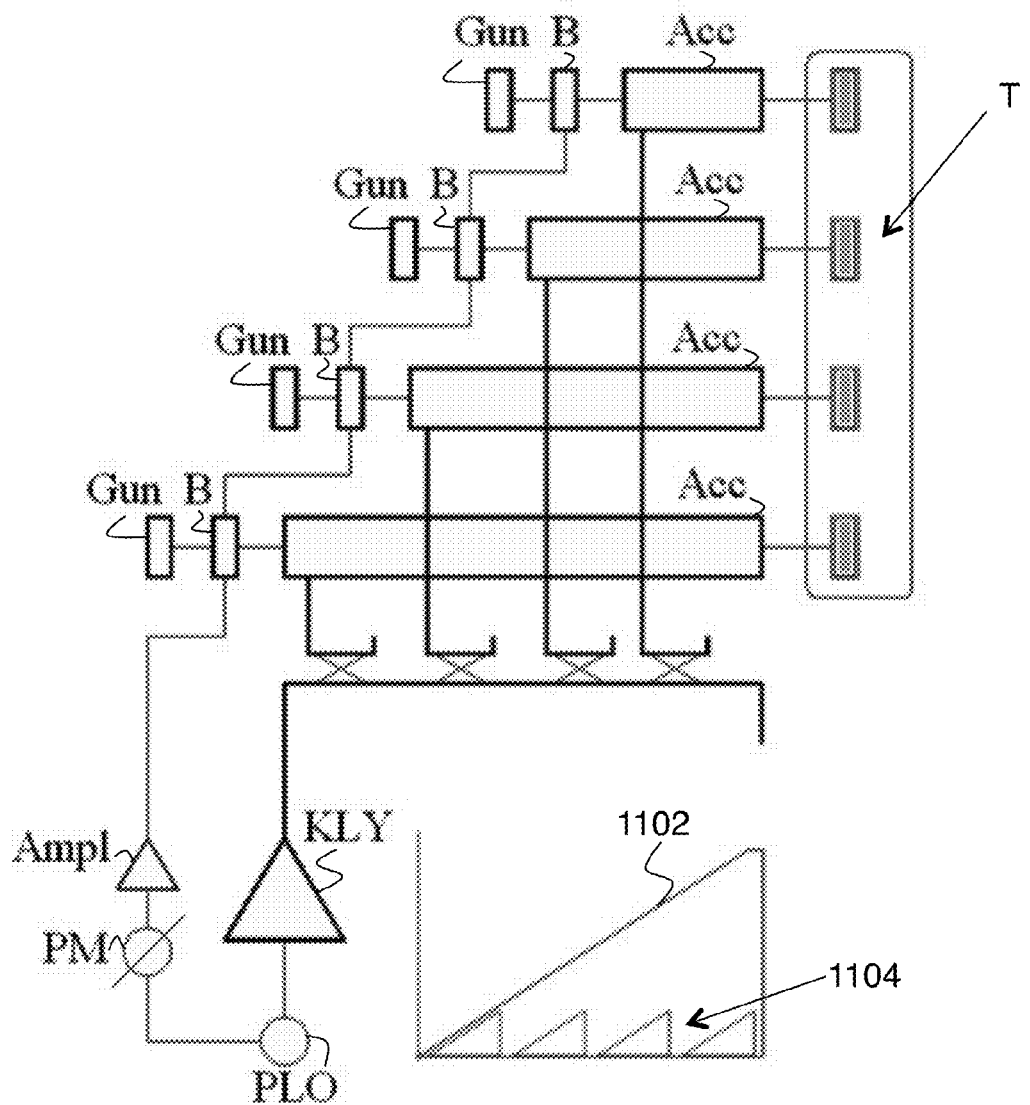
FIG. 11 shows a further multi-target embodiment.

FIG. 11 shows a further multi-target embodiment. Here each accelerator (acc) has its own electron gun (gun) and electron buncher (B). The accelerators are driven by a klystron (KLY) driven by an RF source (PLO). Phase control (PM) is applied to the bunchers via an amplifier (Ampl) to control the relative positioning of the electron bunches and the RF waveforms in the accelerators. Here contributions 1104 from several accelerators contribute to the total output 1102.

Figure 12:
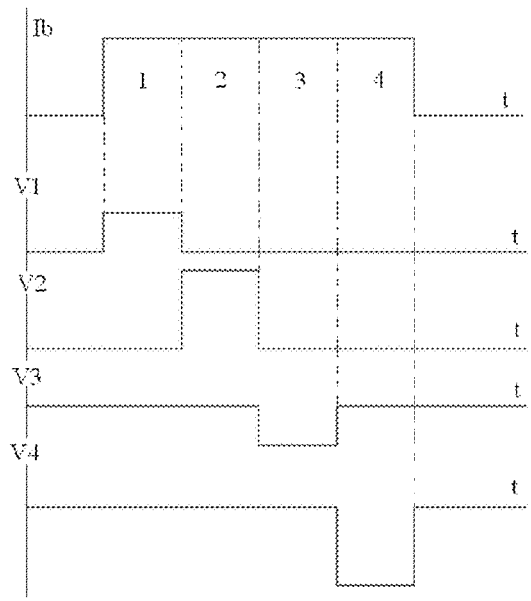
FIG. 12 shows an exemplary timing diagram for four output beam positions.

FIG. 12 shows an exemplary timing diagram for four output beam positions.

Figure 13:
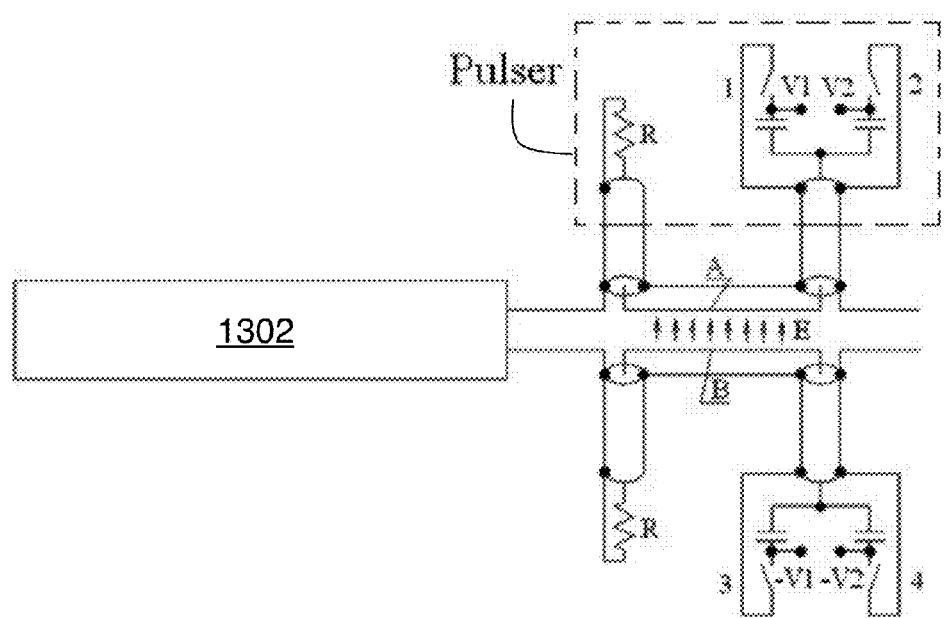
FIG. 13 shows a conceptual approach with a TEM mode kicker for fixed output beam energy.

FIG. 13 shows a conceptual approach with a TEM mode kicker for fixed output beam energy. Here 1302 is a linear accelerator that creates a train of electron bunches, and the circuitry on the right side of the figure acts as the kicker. In practice, a pulser as shown here typically can't switch faster than about 2 ns, so in operation of the pulser, groups of adjacent electron bunches will be routed to the various targets by the pulser, as opposed to the individual routing of electron bunches that is possible with an RF kicker as described above.

Figure 14:
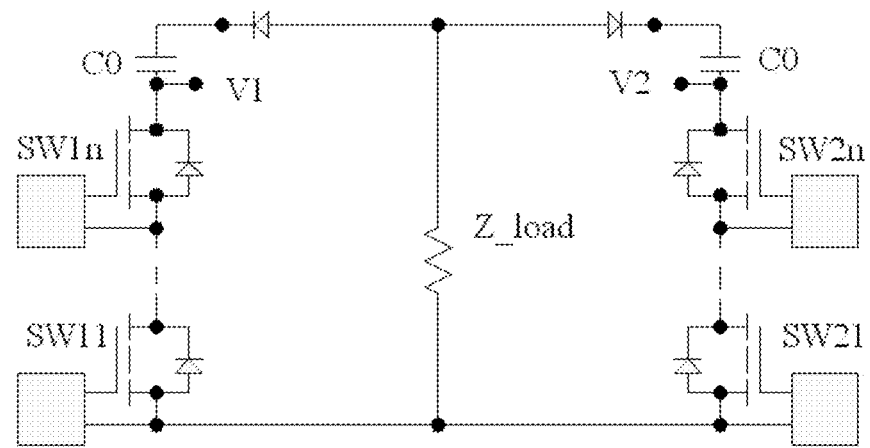
FIG. 14 shows a more detailed schematic of the pulser of FIG. 13.

FIG. 14 shows a more detailed schematic of the pulser of FIG. 13.

The invention claimed is:

1. A method for providing X-ray pulses having a controllable intra-pulse energy distribution, the method comprising:
   providing a periodic train of electron bunches;
   accelerating the electron bunches with a traveling radio frequency (RF) wave in a linear accelerator to provide accelerated electron bunches;
   providing the accelerated electron bunches to one or more targets to generate X-rays, wherein each output X-ray pulse includes contributions from multiple electron bunches; and
   controlling an amplitude of the traveling RF wave and/or a relative phase of the traveling RF wave and the train of electron bunches to control the amount of energy provided to individual electron bunches, thereby providing controllable intra-pulse energy distribution of the output X-ray pulses.

2. The method of claim 1, wherein N is an integer greater than one, wherein N targets are employed, and further comprising:
   separating the accelerated electron bunches with a kicker, wherein a repetition rate of the electron bunches is N times a repetition rate of the kicker, and wherein the kicker periodically distributes incoming electron bunches to the N targets.

3. The method of claim 1, wherein providing a periodic train of electron bunches comprises:
   providing an input electron beam; and
   passing the input electron beam through an electron buncher.

* * * * *